United States Patent
Jafari et al.

(10) Patent No.: US 8,794,234 B2
(45) Date of Patent: *Aug. 5, 2014

(54) INVERSION-BASED FEED-FORWARD COMPENSATION OF INSPIRATORY TRIGGER DYNAMICS IN MEDICAL VENTILATORS

(75) Inventors: Medhi M. Jafari, Laguna Hills, CA (US); Jeffrey K. Aviano, Escondido, CA (US); Edward R. McCoy, Vista, CA (US); Rhomere S. Jimenez, Winchester, CA (US)

(73) Assignee: Covidien LP, Mansfield, MA (US)

( * ) Notice: Subject to any disclaimer, the term of this patent is extended or adjusted under 35 U.S.C. 154(b) by 791 days.

This patent is subject to a terminal disclaimer.

(21) Appl. No.: 12/566,119

(22) Filed: Sep. 24, 2009

(65) Prior Publication Data

US 2010/0071697 A1    Mar. 25, 2010

Related U.S. Application Data

(60) Provisional application No. 61/100,212, filed on Sep. 25, 2008.

(51) Int. Cl.
*A61M 16/00* (2006.01)

(52) U.S. Cl.
USPC ............ 128/204.21; 128/200.24; 128/204.18

(58) Field of Classification Search
USPC ............ 128/200.24, 204.18, 204.21, 204.22, 128/204.23, 204.24, 204.26, 205.11
See application file for complete search history.

(56) References Cited

U.S. PATENT DOCUMENTS

| | | |
|---|---|---|
| 4,752,089 A | 6/1988 | Carter |
| 4,921,642 A | 5/1990 | LaTorraca |
| 4,954,799 A | 9/1990 | Kumar |
| 5,025,806 A | 6/1991 | Palmer et al. |
| 5,052,386 A | 10/1991 | Fischer, Jr. |
| 5,057,822 A | 10/1991 | Hoffman |
| 5,072,737 A | 12/1991 | Goulding |
| 5,103,814 A | 4/1992 | Maher |
| 5,150,291 A | 9/1992 | Cummings et al. |
| 5,161,525 A | 11/1992 | Kimm et al. |
| 5,165,397 A | 11/1992 | Arp |
| 5,237,987 A | 8/1993 | Anderson et al. |
| 5,271,389 A | 12/1993 | Isaza et al. |
| 5,279,288 A | 1/1994 | Christopher |

(Continued)

FOREIGN PATENT DOCUMENTS

EP    1269914    1/2003

OTHER PUBLICATIONS

International Search Report re: PCT-US09-058252, mailed Dec. 17, 2009.

(Continued)

*Primary Examiner* — Annette Dixon

(57) ABSTRACT

A ventilator and method of ventilator control. The ventilator includes a pneumatic system for providing and receiving breathing gas, and a controller operatively coupled with the pneumatic system. The controller employs closed-loop control to provide positive breathing assistance to a patient. Supplemental feed-forward compensatory assistance is also provided, in addition to and independently of that commanded by the closed-loop control. The supplemental assistance may be determined, set or selected based on a ventilator parameter and/or an operator parameter, and/or as an automatic ongoing compensatory mechanism responding to varying patient respiratory demand.

23 Claims, 4 Drawing Sheets

(56) References Cited

U.S. PATENT DOCUMENTS

| | | |
|---|---|---|
| 5,279,549 A | 1/1994 | Ranford |
| 5,299,568 A | 4/1994 | Forare et al. |
| 5,301,921 A | 4/1994 | Kumar |
| 5,307,794 A | 5/1994 | Rauterkus et al. |
| 5,316,009 A | 5/1994 | Yamada |
| 5,319,540 A * | 6/1994 | Isaza et al. ............... 700/41 |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | Latorraca |
| 5,372,126 A | 12/1994 | Blau |
| 5,383,449 A | 1/1995 | Forare et al. |
| 5,385,142 A | 1/1995 | Brady et al. |
| 5,390,666 A | 2/1995 | Kimm et al. |
| 5,394,892 A * | 3/1995 | Kenny et al. ............... 128/897 |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,419,314 A | 5/1995 | Christopher |
| 5,433,193 A | 7/1995 | Sanders et al. |
| 5,437,272 A | 8/1995 | Fuhrman |
| 5,438,980 A | 8/1995 | Phillips |
| 5,443,075 A | 8/1995 | Holscher |
| 5,513,631 A | 5/1996 | McWilliams |
| 5,515,844 A | 5/1996 | Christopher |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,540,225 A | 7/1996 | Schutt |
| 5,540,233 A | 7/1996 | Larsson et al. |
| 5,542,415 A | 8/1996 | Brady |
| 5,544,674 A | 8/1996 | Kelly |
| 5,549,106 A | 8/1996 | Gruenke et al. |
| 5,590,651 A | 1/1997 | Shaffer et al. |
| 5,596,984 A | 1/1997 | O'Mahoney et al. |
| 5,626,151 A | 5/1997 | Linden |
| 5,630,411 A | 5/1997 | Holscher |
| 5,632,269 A | 5/1997 | Zdrojkowski |
| 5,632,270 A | 5/1997 | O'Mahoney et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,676,133 A | 10/1997 | Hickle et al. |
| 5,694,926 A | 12/1997 | DeVries et al. |
| 5,711,294 A | 1/1998 | Kee et al. |
| 5,715,812 A | 2/1998 | Deighan et al. |
| 5,752,509 A | 5/1998 | Lachmann et al. |
| 5,762,480 A | 6/1998 | Adahan |
| 5,771,884 A | 6/1998 | Yarnall et al. |
| 5,775,325 A | 7/1998 | Russo |
| 5,791,339 A | 8/1998 | Winter |
| 5,794,986 A | 8/1998 | Gansel et al. |
| 5,803,065 A | 9/1998 | Zdrojkowski et al. |
| 5,813,399 A | 9/1998 | Isaza et al. |
| 5,819,723 A | 10/1998 | Joseph |
| 5,820,560 A | 10/1998 | Sinderby et al. |
| 5,826,575 A | 10/1998 | Lall |
| 5,829,428 A | 11/1998 | Walters et al. |
| 5,829,441 A | 11/1998 | Kidd et al. |
| 5,830,185 A | 11/1998 | Block, Jr. |
| 5,848,974 A | 12/1998 | Cheng et al. |
| 5,864,938 A | 2/1999 | Gansel et al. |
| 5,865,168 A | 2/1999 | Isaza |
| 5,868,133 A | 2/1999 | DeVries et al. |
| 5,881,717 A | 3/1999 | Isaza |
| 5,881,722 A | 3/1999 | DeVries et al. |
| 5,881,723 A | 3/1999 | Wallace et al. |
| 5,882,348 A | 3/1999 | Winterton et al. |
| 5,884,622 A | 3/1999 | Younes |
| 5,884,623 A | 3/1999 | Winter |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,931,160 A | 8/1999 | Gilmore et al. |
| 5,931,162 A | 8/1999 | Christian |
| 5,934,274 A | 8/1999 | Merrick et al. |
| 5,937,853 A | 8/1999 | Strom |
| 5,937,854 A | 8/1999 | Stenzler |
| 6,013,619 A | 1/2000 | Cochrane et al. |
| 6,024,089 A | 2/2000 | Wallace et al. |
| 6,029,664 A | 2/2000 | Zdrojkowski et al. |
| 6,041,780 A | 3/2000 | Richard et al. |
| 6,047,860 A | 4/2000 | Sanders |
| 6,076,523 A | 6/2000 | Jones et al. |
| 6,086,529 A | 7/2000 | Arndt |
| 6,099,481 A | 8/2000 | Daniels et al. |
| 6,105,572 A | 8/2000 | Shaffer et al. |
| 6,116,240 A | 9/2000 | Merrick et al. |
| 6,116,464 A | 9/2000 | Sanders |
| 6,123,073 A | 9/2000 | Schlawin et al. |
| 6,131,571 A | 10/2000 | Lampotang et al. |
| 6,135,106 A | 10/2000 | Dirks et al. |
| 6,142,150 A | 11/2000 | O'Mahony et al. |
| 6,148,814 A | 11/2000 | Clemmer et al. |
| 6,155,257 A | 12/2000 | Lurie et al. |
| 6,158,432 A | 12/2000 | Biondi et al. |
| 6,158,433 A | 12/2000 | Ong |
| 6,161,539 A | 12/2000 | Winter |
| 6,179,784 B1 | 1/2001 | Daniels et al. |
| 6,220,245 B1 | 4/2001 | Takabayashi et al. |
| 6,240,920 B1 | 6/2001 | Strom |
| 6,257,234 B1 | 7/2001 | Sun |
| 6,269,812 B1 | 8/2001 | Wallace et al. |
| 6,273,088 B1 | 8/2001 | Hillsman |
| 6,273,444 B1 | 8/2001 | Power |
| 6,283,119 B1 | 9/2001 | Bourdon |
| 6,296,630 B1 | 10/2001 | Altman et al. |
| 6,305,373 B1 | 10/2001 | Wallace et al. |
| 6,305,374 B1 | 10/2001 | Zdrojkowski et al. |
| 6,306,099 B1 | 10/2001 | Morris |
| 6,321,748 B1 | 11/2001 | O'Mahoney |
| 6,325,785 B1 | 12/2001 | Babkes et al. |
| 6,354,294 B1 | 3/2002 | Villareal, Jr. |
| 6,355,002 B1 | 3/2002 | Faram et al. |
| 6,357,438 B1 | 3/2002 | Hansen |
| 6,360,740 B1 | 3/2002 | Ward et al. |
| 6,360,745 B1 | 3/2002 | Wallace et al. |
| 6,369,838 B1 | 4/2002 | Wallace et al. |
| 6,371,113 B1 | 4/2002 | Tobia et al. |
| 6,390,091 B1 * | 5/2002 | Banner et al. ............ 128/204.21 |
| 6,412,483 B1 | 7/2002 | Jones et al. |
| 6,439,229 B1 | 8/2002 | Du et al. |
| 6,463,930 B2 | 10/2002 | Biondi et al. |
| 6,467,478 B1 | 10/2002 | Merrick et al. |
| 6,470,888 B1 | 10/2002 | Matter |
| 6,512,938 B2 | 1/2003 | Claure et al. |
| 6,526,970 B2 | 3/2003 | DeVries et al. |
| 6,539,940 B2 | 4/2003 | Zdrojkowski et al. |
| 6,543,449 B1 | 4/2003 | Woodring et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,584,973 B1 | 7/2003 | Biondi et al. |
| 6,615,824 B2 | 9/2003 | Power |
| 6,622,726 B1 | 9/2003 | Du |
| 6,626,843 B2 | 9/2003 | Hillsman |
| 6,629,934 B2 | 10/2003 | Mault et al. |
| 6,631,716 B1 | 10/2003 | Robinson et al. |
| 6,644,310 B1 | 11/2003 | Delache et al. |
| 6,655,382 B1 | 12/2003 | Kolobow |
| 6,662,032 B1 | 12/2003 | Gavish et al. |

(56) References Cited

U.S. PATENT DOCUMENTS

| | | |
|---|---|---|
| 6,668,824 B1 | 12/2003 | Isaza et al. |
| 6,668,829 B2 | 12/2003 | Biondi et al. |
| 6,671,529 B2 | 12/2003 | Claure |
| 6,672,300 B1 | 1/2004 | Grant |
| 6,675,801 B2 | 1/2004 | Wallace et al. |
| 6,718,974 B1 | 4/2004 | Moberg |
| 6,725,447 B1 | 4/2004 | Gilman et al. |
| 6,729,326 B1 | 5/2004 | Winterton et al. |
| 6,739,337 B2 | 5/2004 | Isaza |
| 6,761,165 B2 | 7/2004 | Strickland, Jr. |
| 6,761,167 B1 | 7/2004 | Nadjafizadeh et al. |
| 6,761,168 B1 | 7/2004 | Nadjafizadeh et al. |
| 6,776,156 B2 | 8/2004 | Lurie |
| 6,796,305 B1 | 9/2004 | Banner et al. |
| 6,804,656 B1 | 10/2004 | Rosenfeld et al. |
| 6,810,876 B2 | 11/2004 | Berthon-Jones |
| 6,814,074 B1 | 11/2004 | Nadjafizadeh et al. |
| 6,817,363 B2 | 11/2004 | Biondi et al. |
| 6,820,618 B2 * | 11/2004 | Banner et al. ............ 128/204.23 |
| 6,866,040 B1 | 3/2005 | Bourdon |
| 6,877,511 B2 | 4/2005 | DeVries et al. |
| 6,935,336 B2 | 8/2005 | Lurie et al. |
| 6,948,497 B2 | 9/2005 | Zdrojkowski et al. |
| 6,960,854 B2 | 11/2005 | Nadjafizadeh et al. |
| 6,983,749 B2 | 1/2006 | Kumar et al. |
| 7,017,574 B2 | 3/2006 | Biondi et al. |
| 7,036,504 B2 | 5/2006 | Wallace et al. |
| 7,056,334 B2 | 6/2006 | Lennox |
| 7,066,173 B2 | 6/2006 | Banner et al. |
| 7,077,131 B2 | 7/2006 | Hansen |
| RE39,225 E | 8/2006 | Isaza et al. |
| 7,086,402 B2 | 8/2006 | Peterson |
| 7,100,607 B2 | 9/2006 | Zdrojkowski et al. |
| 7,117,438 B2 | 10/2006 | Wallace et al. |
| 7,210,478 B2 | 5/2007 | Banner et al. |
| 7,222,623 B2 | 5/2007 | DeVries et al. |
| 7,246,618 B2 | 7/2007 | Habashi |
| 7,258,120 B2 | 8/2007 | Melker |
| 7,270,126 B2 | 9/2007 | Wallace et al. |
| 7,314,449 B2 | 1/2008 | Pfeiffer et al. |
| 7,320,321 B2 | 1/2008 | Pranger et al. |
| 7,325,545 B2 | 2/2008 | Dellaca' et al. |
| 7,334,578 B2 | 2/2008 | Biondi et al. |
| 7,341,058 B2 | 3/2008 | Halbert |
| 7,341,061 B2 | 3/2008 | Wood |
| 7,347,205 B2 | 3/2008 | Levi |
| 7,364,553 B2 | 4/2008 | Paz et al. |
| 7,367,335 B2 | 5/2008 | Fuhrman et al. |
| 7,369,757 B2 | 5/2008 | Farbarik |
| 7,370,650 B2 | 5/2008 | Nadjafizadeh et al. |
| 7,395,216 B2 | 7/2008 | Rosenfeld et al. |
| 7,425,201 B2 | 9/2008 | Euliano et al. |
| 7,428,902 B2 | 9/2008 | Du et al. |
| 7,433,732 B1 | 10/2008 | Carney et al. |
| 7,433,827 B2 | 10/2008 | Rosenfeld et al. |
| 7,454,359 B2 | 11/2008 | Rosenfeld et al. |
| 7,460,959 B2 | 12/2008 | Jafari |
| 7,487,773 B2 | 2/2009 | Li |
| 7,487,778 B2 | 2/2009 | Freitag |
| 7,654,802 B2 | 2/2010 | Crawford, Jr. et al. |
| 7,694,677 B2 | 4/2010 | Tang |
| 7,717,113 B2 | 5/2010 | Andrieux |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| 7,984,714 B2 | 7/2011 | Hausmann et al. |
| 7,992,557 B2 | 8/2011 | Nadjafizadeh et al. |
| 8,001,967 B2 | 8/2011 | Wallace et al. |
| 8,021,310 B2 | 9/2011 | Sanborn et al. |
| 8,181,648 B2 | 5/2012 | Perine et al. |
| 8,210,173 B2 | 7/2012 | Vandine |
| 8,210,174 B2 | 7/2012 | Farbarik |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2002/0022823 A1 | 2/2002 | Luo et al. |
| 2002/0026941 A1 | 3/2002 | Biondi et al. |
| 2002/0032430 A1 | 3/2002 | Luo et al. |
| 2002/0091309 A1 | 7/2002 | Auer |
| 2003/0140921 A1 | 7/2003 | Smith et al. |
| 2004/0000314 A1 | 1/2004 | Angel |
| 2004/0077934 A1 | 4/2004 | Massad |
| 2004/0081580 A1 | 4/2004 | Hole et al. |
| 2004/0231664 A1 | 11/2004 | Lurie et al. |
| 2005/0005936 A1 | 1/2005 | Wondka |
| 2005/0034725 A1 | 2/2005 | Stromberg et al. |
| 2005/0039748 A1 | 2/2005 | Andrieux |
| 2005/0109340 A1 | 5/2005 | Tehrani |
| 2005/0121038 A1 | 6/2005 | Christopher |
| 2005/0133027 A1 | 6/2005 | Elaz et al. |
| 2005/0139212 A1 | 6/2005 | Bourdon |
| 2005/0150494 A1 | 7/2005 | DeVries et al. |
| 2005/0154368 A1 | 7/2005 | Lim et al. |
| 2005/0205093 A1 | 9/2005 | Jabour et al. |
| 2005/0217666 A1 | 10/2005 | Fink et al. |
| 2005/0217671 A1 | 10/2005 | Fisher et al. |
| 2006/0065270 A1 * | 3/2006 | Li ............................ 128/204.18 |
| 2006/0089539 A1 | 4/2006 | Miodownik et al. |
| 2006/0107962 A1 | 5/2006 | Ward et al. |
| 2006/0174884 A1 | 8/2006 | Habashi |
| 2006/0201507 A1 | 9/2006 | Breen |
| 2006/0249156 A1 | 11/2006 | Moretti |
| 2006/0271409 A1 | 11/2006 | Rosenfeld et al. |
| 2007/0017515 A1 | 1/2007 | Wallace et al. |
| 2007/0021808 A1 | 1/2007 | Rojas |
| 2007/0023036 A1 | 2/2007 | Grychowski et al. |
| 2007/0068518 A1 | 3/2007 | Urias et al. |
| 2007/0077200 A1 | 4/2007 | Baker |
| 2007/0123785 A1 | 5/2007 | Lu et al. |
| 2007/0129666 A1 | 6/2007 | Barton et al. |
| 2007/0144521 A1 | 6/2007 | DeVries et al. |
| 2007/0162097 A9 | 7/2007 | Rojas |
| 2007/0181122 A1 | 8/2007 | Mulier |
| 2007/0186928 A1 | 8/2007 | Be'Eri |
| 2007/0199566 A1 | 8/2007 | Be'eri |
| 2007/0227537 A1 | 10/2007 | Bemister et al. |
| 2007/0227538 A1 | 10/2007 | Scholler et al. |
| 2007/0255159 A1 | 11/2007 | Tham et al. |
| 2007/0274693 A1 | 11/2007 | Farbarik |
| 2007/0284361 A1 | 12/2007 | Nadjafizadeh et al. |
| 2008/0009761 A1 | 1/2008 | Acker et al. |
| 2008/0011301 A1 | 1/2008 | Qian |
| 2008/0041371 A1 | 2/2008 | Freitag |
| 2008/0041381 A1 | 2/2008 | Tham et al. |
| 2008/0053441 A1 | 3/2008 | Gottlib et al. |
| 2008/0066746 A1 | 3/2008 | Nelson et al. |
| 2008/0066753 A1 | 3/2008 | Martin et al. |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0110461 A1 | 5/2008 | MulQueeny et al. |
| 2008/0125828 A1 | 5/2008 | Ignagni et al. |
| 2008/0135044 A1 | 6/2008 | Freitag et al. |
| 2008/0178880 A1 | 7/2008 | Christopher |
| 2008/0196720 A1 | 8/2008 | Kollmeyer et al. |
| 2008/0214947 A1 | 9/2008 | Hunt et al. |
| 2008/0230065 A1 | 9/2008 | Heinonen |
| 2008/0236582 A1 | 10/2008 | Tehrani |
| 2008/0295839 A1 | 12/2008 | Habashi |
| 2008/0295840 A1 | 12/2008 | Glaw |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |

(56) References Cited

U.S. PATENT DOCUMENTS

| | | |
|---|---|---|
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1* | 10/2009 | Jafari et al. ............ 128/205.25 |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023879 A1 | 2/2011 | Vandine et al. |
| 2011/0041849 A1 | 2/2011 | Chen et al. |
| 2011/0259330 A1 | 10/2011 | Jafari et al. |

OTHER PUBLICATIONS

7200 Series Ventilator, Options, and Accessories: Operators Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

* cited by examiner

INVERSION-BASED FEED-FORWARD COMPENSATION OF INSPIRATORY TRIGGER DYNAMICS IN MEDICAL VENTILATORS

RELATED APPLICATION

This application claims the benefit of U.S. Provisional Application No. 61/100,212 filed Sep. 25, 2008, which application is hereby incorporated herein by reference.

BACKGROUND

The present description pertains to ventilator devices used to provide breathing assistance. Modern ventilator technologies commonly employ positive pressure to assist patient-initiated inspiration (inhalation). For example, after detecting that the patient wants to inhale, the ventilator control systems track a reference trajectory to increase pressure in an inhalation airway connected to the patient, causing or assisting the patient's lungs to fill. The tracking fidelity of the generated pressure (compared against the desired reference trajectory) and timely delivery of demanded flow are important factors impacting patient-ventilator synchrony and patient's work of breathing. Upon reaching the end of the inspiration, the patient is allowed to passively exhale and the ventilator controls the gas flow through the system to maintain a designated airway pressure level (PEEP) during the exhalation phase.

Modern ventilators typically include microprocessors or other controllers that employ various control schemes. These control schemes are used to command a pneumatic system (e.g., valves) that regulates the flow rates of breathing gases to and from the patient. Closed-loop control is often employed, using data from pressure/flow sensors.

Generally, it is desirable that the control methodology cause a timely response to closely match the desired quantitative and timing requirements of the operator-set ventilation assistance. However, a wide range of variables can significantly affect the way ventilator components respond to commands issued from the controller to generate the intended pressure waveform. For example, the compliance of the patient breathing circuit, the mechanical and transient characteristics of pneumatic valves, the resistance of the circuit to gas flow, etc. and patient's breathing behavior can cause significant variation or delays in the resulting pressure/flow waveforms compared to the desired reference. Furthermore, even when very specific situational information is available (e.g., concerning patient and device characteristics), existing control systems are often sub-optimal in leveraging this information to improve ventilator performance.

DETAILED DESCRIPTION

Figure 1:
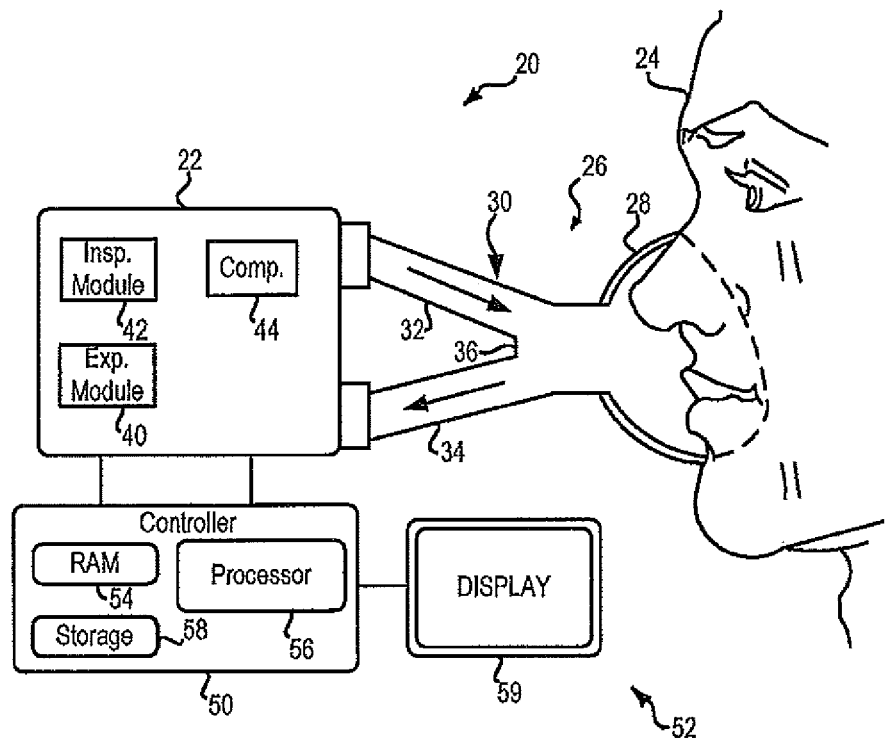
FIG. 1 is a schematic depiction of a ventilator.

FIG. 1 depicts a ventilator 20 according to the present description. As will be described in detail, the various ventilator embodiments described herein may be provided with improved control schemes. These control schemes typically enhance closed-loop control performance, and may be operator-selected to account for specific factors relating to the device, patient and/or use setting. When implemented for spontaneous breathing, the control methodologies normally command a specified ventilatory support following detection of patient inspiratory effort. This compensatory support is in addition to that commanded by the primary closed-loop control system, and its application improves response time, patient-ventilator synchrony and other aspects of system performance. The compensatory support is (model) inversion-based and computed from known and/or estimated hardware and/or patient characteristics model(s) and measured parameters of breathing behavior. After determination of the quantity and temporal waveform of the compensation, it is delivered by feedforward mechanism as an added component to the desired signal reference trajectory generated by the ventilator's closed-loop controller. Also, it is envisioned that a compensatory mechanism could be designed based on the same concept and adapted as a transitory augmentation to the actuator command. The present discussion will focus on specific example embodiments, though it should be appreciated that the present systems and methods are applicable to a wide variety of ventilatory devices.

Referring now specifically to FIG. 1, ventilator 20 includes a pneumatic system 22 for circulating breathing gases to and from patient 24 via airway 26, which couples the patient to the pneumatic system via physical patient interface 28 and breathing circuit 30. Breathing circuit 30 typically is a two-limb circuit having an inspiratory limb 32 for carrying gas to the patient, and an expiratory limb 34 for carrying gas from the patient. A wye fitting 36 may be provided as shown to couple the patient interface to the two branches of the breathing circuit. The present description contemplates that the patient interface may be invasive or non-invasive, and of any configuration suitable for communicating a flow of breathing gas from the patient circuit to an airway of the patient. Examples of suitable patient interface devices include a nasal mask, nasal/oral mask (which is shown in FIG. 1), nasal prong, full-face mask, tracheal tube, endotracheal tube, nasal pillow, etc.

Pneumatic system 22 may be configured in a variety of ways. In the present example, system 22 includes an expiratory module 40 coupled with expiratory limb 34 and an inspiratory module 42 coupled with inspiratory limb 32. Compressor 44 is coupled with inspiratory module 42 to provide a gas source for controlled ventilatory support via inspiratory limb 32.

The pneumatic system may include a variety of other components, including air/oxygen supply sources, mixing modules, valves, sensors, tubing, accumulators, filters, etc.

Controller 50 is operatively coupled with pneumatic system 22, and an operator interface 52 may be provided to enable an operator to interact with the ventilator (e.g., change ventilator settings, select operational modes, view monitored parameters, etc.). Controller 50 may include memory 54, one or more processors 56, storage 58, and/or other components of the type commonly found in measurement, computing, and command and control devices. As described in more detail below, controller 50 issues commands to pneumatic system 22 in order to control the breathing assistance provided to the patient by the ventilator. The specific commands may be based on inputs sensed/received from patient 24, pneumatic system 22 including transducers and data acquisition modules, operator interface 52 and/or other components of the ventilator. In the depicted example, operator interface includes a display 59 that is touch-sensitive, enabling the display to serve both as an input and output device.

Figure 2:
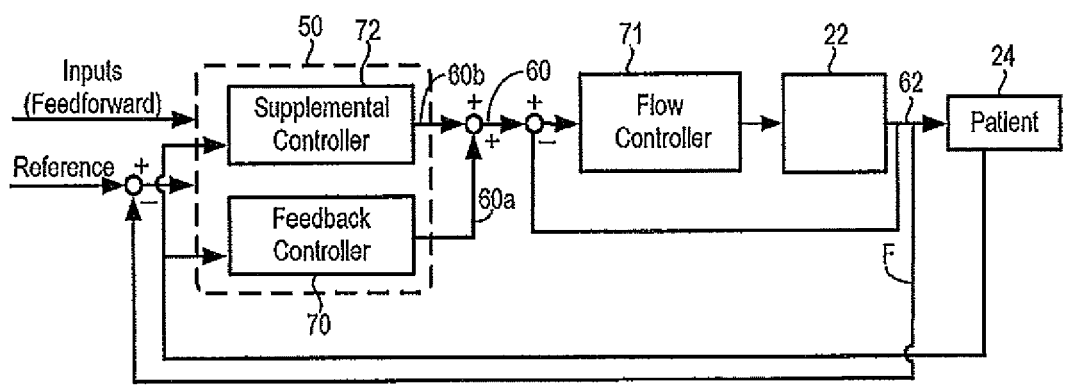
FIG. 2 schematically depicts control systems and methods that may be employed with the ventilator of FIG. 1.

FIG. 2 schematically depicts exemplary systems and methods of ventilator control. As shown, controller 50 issues control commands 60 to ultimately drive pneumatic system 22 and thereby regulate circulation (delivery and exhaust) of breathing gas to and from patient 24. The command(s) 60 to the Flow Controller 71 and ultimately to the pneumatic system actuator(s) to regulate flow rates of different gases such as air and/or oxygen (as applicable based on set mix ratio) is (are) calculated and combined based on two methods: closed-loop control of the output signal and inversion-based compensatory feedforward. For example, in the case of a spontaneously breathing patient on Pressure Support, the closed-loop control system may be envisioned to consist of a closed-loop pressure controller in cascade with closed-loop flow controller 71 (more than one flow controller in cases when flow rates of more than one gas need to be regulated). In this example, at every control cycle (e.g., every 5 ms) the closed-loop pressure controller computes a flow rate command based on the measured pressure error derived from a comparison against the desired pressure trajectory. The Supplemental Controller 50, under this example, utilizes an inversion-based method to compute from known and/or estimated hardware models (breathing circuit resistance and compliance, actuator dead bands and delays, etc.) and/or patient characteristics (respiratory resistance and compliance) or measured parameters of breathing behavior (e.g., estimated pressure drop caused by patient inspiratory effort), or controller delays to determine the quantity and temporal waveform of the compensation and calculates the corresponding command (in this example, the supplemental flow rate) for each control cycle. In this example, the additional (flow) command is added to the desired flow reference command generated by the pressure controller. The combined Supplemental flow command 60b and pressure Controller flow command 60a constitutes the reference input 60 to the flow controller 71. In general, in the case of Pressure Support, the closed-loop controller may be designed in different ways and as an example it could consist of a single pressure controller combined with a mix controller that closes the loop on the measured pressure signal. In this case or other closed-loop control design variations, the nature of the compensatory feedforward supplement would be determined in compliance with the physical units of the resulting command.

Figure 3:
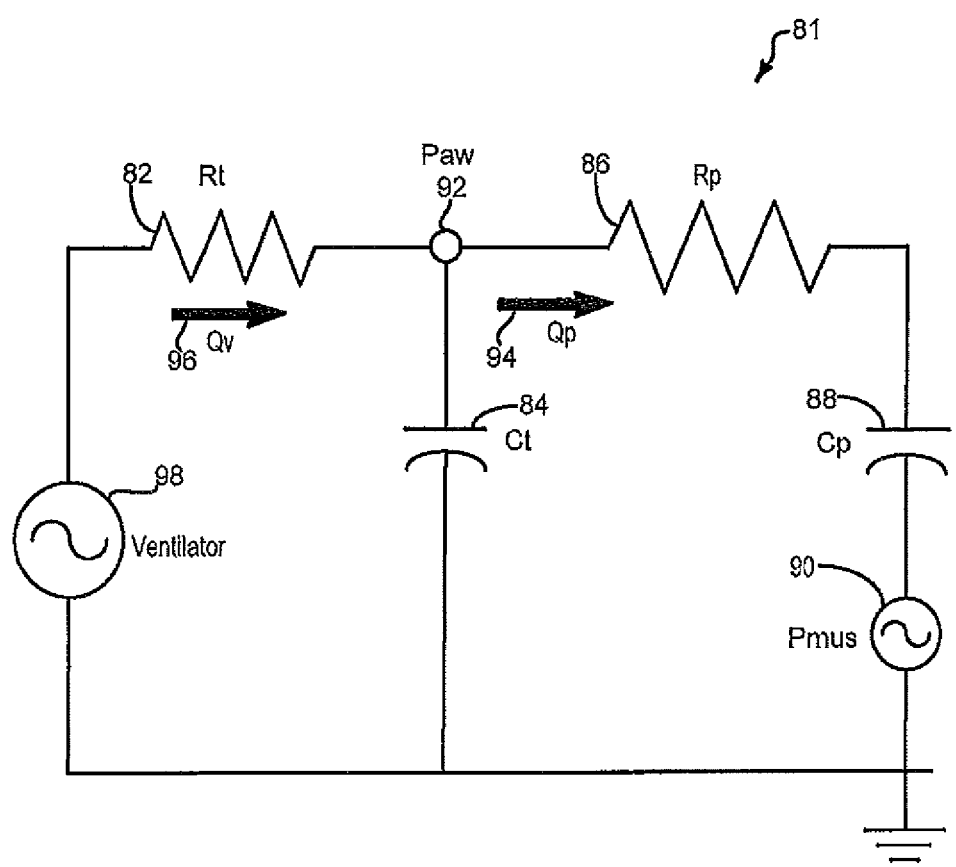
FIG. 3 schematically depicts an exemplary lumped parameter model which may be used to derive supplemental control commands shown in FIGS. 4B, 4C and 4D.

FIG. 3 represents a simplified lumped-parameter analog model 81 for patient circuit and single-compartment respiratory system. Patient circuit is represented by resistance Rt 82 and compliance Ct 84. The patient's respiratory dynamics are captured by total respiratory resistance Rp 86, total respiratory compliance Cp 88, and patient-generated muscle pressure Pmus 90. Using this model, the time response of the airway pressure Paw 92 is a function of patient muscle pressure Pmus 90 and lung flow Qp 94 subsequent to ventilator output flow Qv 96 as determined and delivered by a ventilator 98 command and control subsystems and ventilator-patient interactive characteristics. In patient-initiated triggering, the airway pressure drops below the baseline and lung flow increases concomitantly as a result of the patient's inspiratory effort and the negative pressure generated in the lung. The current embodiment may employ this model as the inversion mechanism to compute an optimum additional volume of gas to be feed-forward as a supplement to the flow rates determined by the closed-loop controller. The additional volume will be commanded independent of the closed-loop pressure regulation controller and delivered in accordance with a specified flow time trajectory. During the patient triggering process, the pressure drop generated by the patient effort will be indicated by a corresponding pressure drop at the patient wye and increasing flow into the lung. To bring back the lung pressure to the baseline level at the initial phase of an inspiration, one way to compute the volume of gas required to be added into the lung would be to estimate the lung pressure, $$P_{lung} = P_{aw} - R_p * Q_p,$$

then, calculate the drop from baseline, and finally compute the additional volume using a given or an estimated value for lung compliance:

$$\Delta V = \Delta P * C_p$$

In this example, the proposed algorithmic process may consist of two basic steps:

1. The wye (proximal patient-circuit interface) pressure and lung flow waveforms during the triggering process leading to the ventilator's successful transition into inspiration may be used in conjunction with the estimated ventilator-plant parameters (including actuator and controller time delays and patient respiratory mechanics) and patient comfort considerations to compute an optimum gas volume to be supplemented as an added flow rate over time to the flow determined by the closed-loop controller(s). The feedforward flow is intended to enhance more effective pressure recovery to the designated baseline and thus minimizing the patient's triggering work of breathing and enhancing comfort.

2. The compensatory volume will be commanded independent of the closed-loop pressure regulation controller and delivered in accordance with a specified flow time trajectory. This trajectory will consist of two sections: an initial step of amplitude (Qaddmax) and duration Tstep 76 initiated immediately after trigger detection and followed by a final exponential drop from Qaddmax plateau to zero by a specified time constant Tauexp 78, shown in FIGS. 4B-4D. These parameters may be set adaptively based on patient breathing behavior and ventilator performance or optimum fixed values could be determined to enable satisfactory performance for each patient type. The ultimate goal would be to minimize the work or triggering, minimize tracking error, and ensure patient comfort and patient-ventilator synchrony.

The depicted schematic interaction between pneumatic system 22 and patient 24, as shown in FIG. 1 and FIG. 2, may be viewed in terms of pressure or flow "signals." For example, signal 62 may be an increased pressure which is applied to the patient via inspiratory limb 32. Control commands 60 are based upon inputs received at controller 50 which may include, among other things, inputs from operator interface 52, and feedback from pneumatic system 22 (e.g., from pressure/flow sensors) and/or sensed from patient 24.

Controller 50, as shown in FIG. 1 and FIG. 2, may be configured to implement a wide variety of control methodologies, though the present examples have proved particularly useful in the context of patient-triggered pressure-based ventilation. In particular, ventilator 20 is adapted to detect inspiratory efforts of patient 24, and respond by delivering positive pressure to assist the breathing effort. Magnitude, timing and other characteristics of the positive pressure assist may be controlled in response to feedback received from the device (e.g., user interface 59, pneumatic system 22) or patient 24. In many cases, patient feedback is inferred from device data. For example, a relatively rapid pressure drop at the patient interface 36 may be used to infer an inspiratory patient effort. The magnitude of this pressure drop together with patient's respiratory mechanics parameters (given or estimated) and breathing circuit characteristics could be used to estimate the gas volume required to be added into the lung to bring back the lung pressure to the baseline.

Ventilator control may be further understood with reference to FIG. 4A-4D. FIG. 4A shows several cycles of typical tidal breathing, in terms of lung flow and airway pressure. As discussed above, a patient may have difficulty achieving normal tidal breathing, due to illness or other factors. In some cases, normal lung volumes may be achieved without mechanical ventilation, but only with debilitating effort that can impede healing or cause further physiological damage. In other cases, disease factors prevent the patient from achieving tidal volumes without assistance.

Regardless of the particular cause or nature of the underlying condition, ventilator 20 typically provides breathing assistance via positive pressure during inspiration. FIGS. 4B-4D show example control signal waveforms, to be explained in more detail below, that may be used to drive pneumatic system 22 to deliver the desired pressure support. In many cases, the goal of the control system is to deliver a controlled pressure profile or trajectory (e.g., pressure as a function of time) during the inspiratory or expiratory phases of the breathing cycle. In other words, control is performed to achieve a desired time-varying pressure output 62 from pneumatic system 22, with an eye toward achieving or aiding breathing.

As shown in FIG. 2, controller 50 includes a primary controller 70, also referred to as the "feedback" controller, that generates command 60a intended to target the desired reference trajectory, and a supplemental controller 72 to augment the closed loop control with command 60b and proactively compensate for system latencies caused by multiple factors as discussed above. The compensatory quantity and its temporal delivery characteristics are determined based on specific operational settings, to enhance patient-ventilator synchrony and control system dynamic effectiveness.

For a given respiratory therapy, the treatment goal is often set in terms of the timing and amount of increased pressure and gas mixture delivered to the patient during inspiration and maintenance of a set airway pressure during exhalation. Accordingly, a design focus of the control system should be to quickly and accurately detect the beginning of the patient's attempted inspiration, and then have the mechanical system rapidly respond to track the desired pressure trajectory with optimum fidelity.

As shown in FIG. 2, controller 70 is designed to provide such closed-loop control. In particular, controller 50 detects airway pressure (e.g., via feedback signal F) drop from baseline (Pressure Triggering mechanism) or increased lung flow (Flow Triggering mechanism) to establish initiation of inspiratory support. Closed-loop controller 70 and supplemental controller 72 then work in concert to command pneumatic system 22 to provide the desired inspiratory signal trajectory.

As will be described in more detail below, the provision of a supplemental control enables the operator of the ventilator to more accurately account and compensate for various factors affecting system dynamics in a more timely fashion. For example, pneumatic system 22 contains many components that can significantly affect the response produced by a given control command, such as command 60a. Further, the patient constitutes a major variable whose time-varying and hard-to-predict breathing behavior is unknown to typical ventilator closed-loop controllers and would cause variations and latencies in the controller's tracking performance.

In particular, pneumatic system 22 typically includes multiple modules, each having various components. Valve characteristics, the geometry and compliance of pneumatic passages, conduit resistance to gas flow, actuator/controller time delays, humidifier parameters, filter types and a host of other factors can affect system dynamics. In particular, these components can create variable lags, such that the pressure in inspiratory limb 32 may rise more slowly than desired. This lagging of the desired trajectory would require the patient to do more breathing work during inspiration, and thereby may negatively impact treatment.

A number of patient characteristics and breathing behavior can also affect the system's dynamic performance. The patient characteristics may define or describe physiological traits of the patient, including respiratory musculature, baseline or expected respiratory performance, height, weight, specific disease/illness indications, age, sex, etc.

Closed-loop controller 70 may employ various control schemes, and typically is designed to command the output to a desired value or trajectory without addition of any model-based feedforward supplemental control regimes computed based on the inversion of the ventilator-patient model under ongoing dynamic conditions using available measurements. However, due to the nature of the closed loop control and the potential wide variation in device and patient characteristics, signal 60a may produce sub-optimal pressure response and/or patient-device synchrony. Accordingly, supplemental controller 72 may provide an additional command signal 60b to substantially decrease the patient work effort during inspiration, allowing the breathing assistance provided by the ventilator to be properly synchronized with the patient initiated breathing cycle. As one example, command signal 60b may be generated using a feed-forward predictive model, to be discussed in more detail herein, which leverages a richer data set concerning the device and/or patient to fine tune ventilator performance.

Indeed, command signal 60b may take into account plant parameters, such as delays caused by ventilator components, and/or patient parameters affecting system transfer functions. In this way proper triggering can occur and the performance of the overall pneumatic system can be better synchronized with the respiratory cycle of the patient. Signal 60b typically is not intended to be used as the primary control strategy. Rather, it provides an additional feed-forward input to minimize delays and otherwise fine tune controller tracking fidelity during inspiration. Because the supplementary command acts as an adjunct to the primary closed-loop controller, instead of replacing it, the primary closed-loop feature would protect against delivery of excessively high commands. In other words, even though the added control is feed-forward and independent of the closed-loop controller, the ultimate output flow to the patient is regulated by the closed-loop regime, i.e., at every control cycle (e.g., 5 ms), the contribution of the feedback controller to the total command would be promptly reduced in case of output deviation caused by the supplemental command.

FIGS. 4B, 4C and 4D show exemplary control waveforms that may be provided by the supplemental feed-forward controller 72. The different supplemental waveforms 60b1, 60b2 and 60b3 are alternatives that may be selected for different circumstances. In other words, supplemental command 60b1 might be applied in a first operational environment, with supplemental command 60b2 being used in a different operational environment, for example on a patient with a different breathing characteristic or type of illness (when available). In each of the three examples, the supplemental command is provided rapidly upon detection of the trigger (patient initiates in-breath), and the signal waveform may be described in terms of three aspects. The first aspect is gain or rise 74. The gain may be a simple step-up to the maximum flow rate Qmax, as shown in FIG. 4B and FIG. 4C. In another example, the gain may occur over time, as shown in FIG. 4D. Accordingly, the gain may be described in terms of magnitude Qmax and time. The second aspect, Tstep 76, is the amount of time over which Qmax is delivered. A third aspect is the exponential decay trajectory time constant Tauexp 78.

These control signal aspects may be modified as necessary to achieve control design and ultimately treatment objectives. In one example, the patient may periodically generate a larger inspiratory effort and demand an increased tidal volume and duration of the breathing cycle. To account for these variations, Qmax and Tstep, or Tauexp may be adjusted accordingly. Alternatively, the shape of the waveform generated by the supplemental controller 72 may be trapezoidal, sawtooth or have other forms. The specific waveform 60b1, 60b2, 60b3 (or others) typically is selected based on desired output of the system and to account for device and patient characteristics.

The systems and methods described herein may employ this model as an inversion mechanism to compute an optimum additional volume of gas to be feed-forward as a supplement to the flow rates commanded by the primary controller 70. As further described herein, the additional volumes are determined independently of the closed-loop pressure regulation controller (controller 70) and in accordance with a specified flow time trajectory (see supplemental commands 60b1, 60b2, etc.)

The values of the various lumped-parameters may be calculated based on data associated with the ventilator device, patient, operational setting, and ongoing pressure and flow measurements, etc. For example, inputs into operator interface 52 may be used to set values for the lumped parameters. Then, during operation of the ventilator, the supplemental controller calculates compensatory regimes to be feed-forward and commanded by the primary flow controller 71.

In other examples, the model may be expanded to include additional components to model further aspects of the patient-ventilator system. Alternatively, other types of predictive modeling may be used to synchronize the ventilator with the patient's breathing cycle and improve system response.

Figure 4:
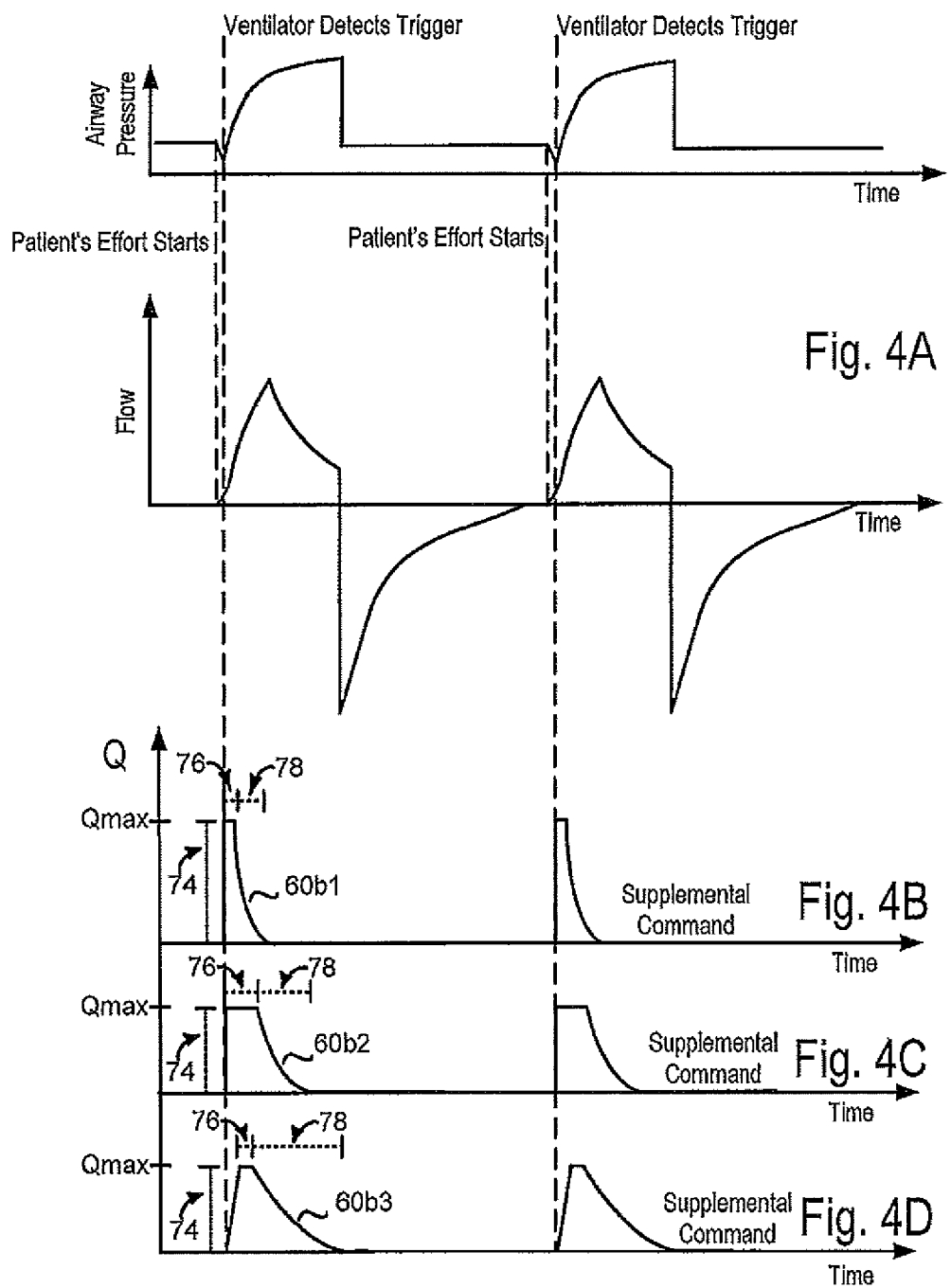
FIGS. 4A-4D depict exemplary tidal breathing in a patient, and examples of control commands which may be employed in a ventilator to assist tidal breathing with inspiratory pressure support.

As shown in FIG. 4, the control enhancement provided by supplemental controller 72 may take various forms. For example, commands 60b may be selected differently in order to provide different pressure trajectory enhancements, such as faster rise time, pressure boosts of varying magnitude/duration, etc. In various example embodiments, ventilator 20 may be configured to allow an operator to select control enhancement via interaction with operator interface 52. For example, selection of a first parameter or parameter combination might cause controller 72 to produce commands 60b1, while a second parameter/combination might produce commands 60b2 and so on.

Figure 5:
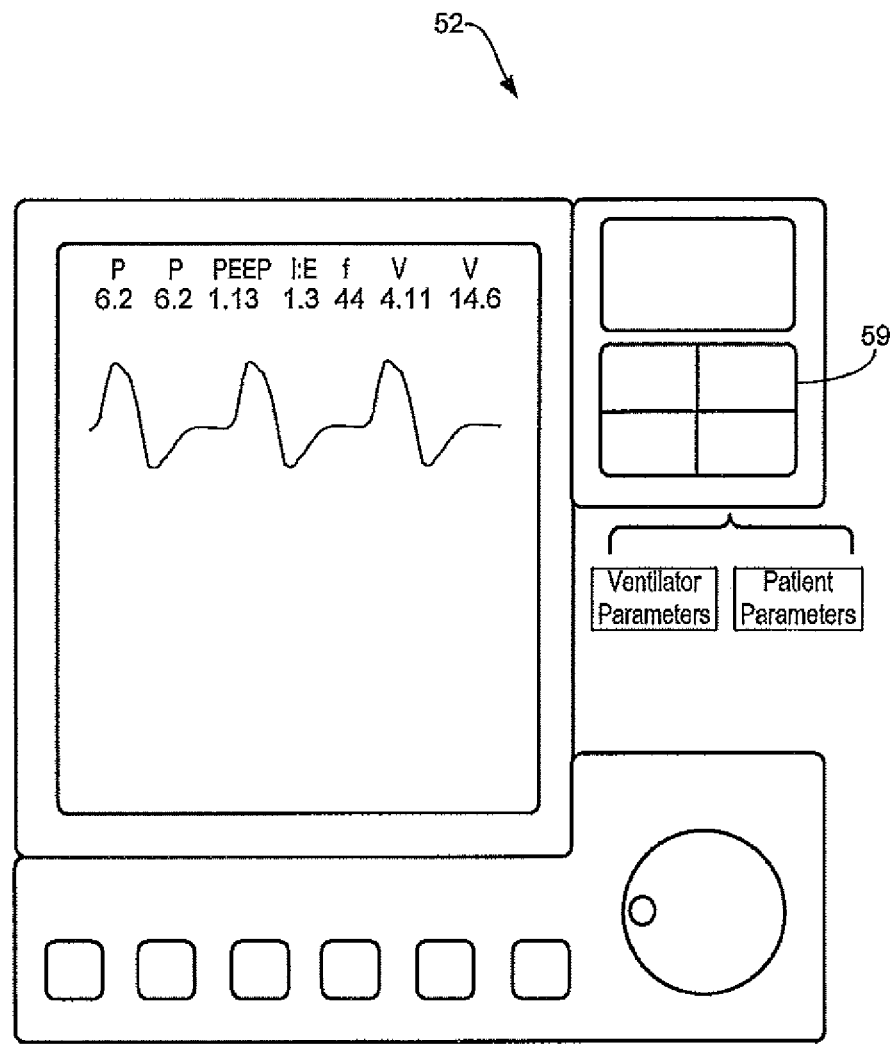
FIG. 5 depicts a touch-sensitive display interface that may be used with the ventilator of FIG. 1.

FIG. 5 schematically depicts an exemplary interface scheme for selecting various parameters to control operation of supplemental controller 72. The depicted exemplary scheme may be applied to the controller through various input/interface mechanisms, including through use of operator interface 52. For example, touch-sensitive display 59 may include a high-level menu option, as indicated, for entering a portion of the interface where specific supplemental control parameters can be selected. As indicated, the operator may be permitted to select ventilator/device parameters and/or parameters associated with the patient. As indicated ventilator/device parameters may include type of patient interface; etc. Patient parameters may include information concerning respiratory dynamics; respiration rates; patient physiological data; specification of whether the patient is adult, pediatric, neonatal, etc.; whether disease factors A, B and/or C, etc. are present. These are but a few of the many possible parameters that can be selected (e.g., by an operator) or estimated online by the ventilator to tune the feed-forward trajectories commanded by supplemental controller 72. The main parameters to consider in conjunction with the lumped-parameter model are: tubing characteristics (resistance, compliance), patient respiratory mechanics (resistance, compliance), actuator dead bands and controller delays.

A variety of advantages may be obtained through use of the exemplary control systems and methods described herein. Respiratory therapy can be effectively improved through provision of the independent enhanced controller 72, because it provides an operator tunable and/or patient-interactive model-based mechanism for enriching the parameter set used to control the ventilatory assistance. In particular, a multitude of additional ventilator and patient variables may be selected to tune the controller and improve the fidelity with which the system tracks the desired output trajectory. The resulting speed and fidelity improvements lead to better synchrony of the device with the patient's spontaneous breathing operation, a key measure of ventilator performance. Furthermore, since the primary closed-loop control system still constrains system output, integration of the enhanced supplemental control typically will not pose system overshoot or stability problems.

It will be appreciated that the embodiments and method implementations disclosed herein are exemplary in nature, and that these specific examples are not to be considered in a limiting sense, because numerous variations are possible. The subject matter of the present disclosure includes all novel and nonobvious combinations and subcombinations of the various configurations and method implementations, and other features, functions, and/or properties disclosed herein. Claims may be presented that particularly point out certain combinations and sub combinations regarded as novel and nonobvious. Such claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

What is claimed is:

1. A ventilator, comprising:
   a pneumatic system for providing and receiving breathing gas;
   a controller operatively coupled with the pneumatic system; and
   an operator interface, where the controller is operable to:
   execute a control scheme to command the pneumatic system to provide breathing gas to a patient during inspiration, where such breathing gas is provided in response to the ventilator detecting that the patient is attempting to initiate inspiration; and
   command delivery of a feed-forward input of additional breathing gas corresponding to a desired boost pressure waveform to the patient during inspiration, where the feed-forward input is commanded in response to operator selection of at least one of a ventilator parameter and a patient parameter at the operator interface, and where the desired boost pressure waveform is continuously modeled based on performance measurements of the control scheme by adjusting a gain and at least one of an amount of time required to deliver a maximum flow and an exponential decay trajectory time constant.

2. The ventilator of claim 1, where the patient parameter enables specification of patient age.

3. The ventilator of claim 2, where the patient parameter enables specification that the patient is an adult patient.

4. The ventilator of claim 2, where the patient parameter enables specification that the patient is a pediatric patient.

5. The ventilator of claim 2, where the patient parameter enables specification that the patient is a neonatal patient.

6. The ventilator of claim 1, where the patient parameter enables specification of a patient disease condition.

7. The ventilator of claim 1, where the patient parameter enables specification of a physiological characteristic of the patient.

8. The ventilator of claim 1, where the ventilator parameter enables specification of characteristics of airway components used to couple the patient to the pneumatic system.

9. The ventilator of claim 1, where the ventilator parameter enables specification of characteristics of the pneumatic system.

10. A ventilator, comprising:
a pneumatic system for providing and receiving breathing gas; and
a controller operatively coupled with the pneumatic system, where the controller is operable to:
execute a control scheme to command the pneumatic system to provide breathing gas to a patient during inspiration;
receive a baseline closed-loop input corresponding to a desired output pressure of breathing gas from the pneumatic system;
receive an additional feed-forward input corresponding to a desired boost pressure waveform to be added to the desired output pressure, the additional feed-forward input being dependent upon at least one of an operator-selected ventilator parameter and an operator-selected patient parameter;
detect patient initiation of an inspiratory phase of a respiration cycle; and
during the inspiratory phase, command the pneumatic system to provide breathing gas based on the closed-loop input and the additional feed-forward input, the breathing gas being constrained through application of a feedback signal to the controller, where the desired boost pressure waveform is continuously modeled based on performance measurements of the control scheme by adjusting a gain and at least one of an amount of time required to deliver a maximum flow and an exponential decay trajectory time constant.

11. The ventilator of claim 10, further comprising an operator interface operatively coupled with the controller and configured to enable an operator to select at least one ventilator parameter and patient parameter.

12. The ventilator of claim 10, further comprising a patient breathing circuit and a physical patient interface configured to couple a patient to the pneumatic system.

13. The ventilator of claim 10, where the patient parameter includes specification of patient age.

14. The ventilator of claim 13, where the patient parameter includes specification that the patient is an adult patient.

15. The ventilator of claim 13, where the patient parameter includes specification that the patient is a pediatric patient.

16. The ventilator of claim 13, where the patient parameter includes specification that the patient is a neonatal patient.

17. The ventilator of claim 10, where the patient parameter includes specification of a patient disease condition.

18. The ventilator of claim 10, where the patient parameter includes specification of a physiological characteristic of the patient.

19. The ventilator of claim 10, where the ventilator parameter includes specification of characteristics of airway components used to fluidly couple the patient to the pneumatic system.

20. The ventilator of claim 10, where the ventilator parameter includes specification of characteristics of the pneumatic system.

21. A method of operating a patient-triggered, positive pressure ventilator, comprising:
driving a pneumatic system of the ventilator with a closed-loop control regime to provide positive pressure breathing assistance during inspiration;
providing a supplemental added pressure boost corresponding to a desired boost pressure waveform during inspiration in addition to the breathing assistance commanded by the closed-loop control regime; and
setting the supplemental added pressure boost based on operator input of at least one of a ventilator parameter and a patient parameter, where the desired boost pressure waveform is continuously modeled based on performance measurements of the closed-loop control regime by adjusting a gain and at least one of an amount of time required to deliver a maximum flow and an exponential decay trajectory time constant.

22. The method of claim 21, where the supplemental added pressure boost is applied during each of a plurality of respiration cycles, subsequent to patient-triggering of inspiration.

23. The method of claim 21, where the supplemental added pressure boost is tunable from one therapy session to the next, such that in a first therapy session, the positive pressure breathing assistance supplied by the closed loop-control regime is supplemented with a first supplemental added pressure boost, while during a second therapy session, the positive pressure breathing assistance supplied by the closed loop-control regime is supplemented with a second supplemental added pressure boost which is different from the first, such difference being based on a change in at least one of the ventilator parameter and the patient parameter.

* * * * *